United States Patent
Oda

(10) Patent No.: US 11,850,085 B2
(45) Date of Patent: Dec. 26, 2023

(54) DISPLAY DEVICE AND CONTROL PROGRAM

(71) Applicant: FUJIFILM CORPORATION, Tokyo (JP)

(72) Inventor: Yoshinari Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 295 days.

(21) Appl. No.: 17/486,956

(22) Filed: Sep. 28, 2021

(65) Prior Publication Data

US 2022/0096038 A1 Mar. 31, 2022

(30) Foreign Application Priority Data

Sep. 30, 2020 (JP) ................. 2020-166470

(51) Int. Cl.
*A61B 6/00* (2006.01)
*A61B 6/04* (2006.01)

(52) U.S. Cl.
CPC .............. *A61B 6/54* (2013.01); *A61B 6/0414* (2013.01); *A61B 6/462* (2013.01); *A61B 6/463* (2013.01); *A61B 6/502* (2013.01)

(58) Field of Classification Search
CPC ....... A61B 6/502; A61B 6/0414; A61B 6/025; A61B 6/4291; A61B 90/17; A61B 6/0435; A61B 6/04; A61B 5/4312; A61B 5/0091; A61B 90/39; A61B 8/403; A61B 5/708; A61B 6/461; A61B 6/547; A61B 2018/00333; A61B 5/742; A61B 6/465; A61B 6/584; A61B 5/743; A61B 6/0407;

(Continued)

(56) References Cited

U.S. PATENT DOCUMENTS

2005/0063509 A1 3/2005 Defreitas et al.
2008/0087830 A1 4/2008 Kashiwagi
(Continued)

FOREIGN PATENT DOCUMENTS

JP 2004-173891 A 6/2004
JP 2008-086389 A 4/2008
(Continued)

OTHER PUBLICATIONS

English language translation of the following: Office action dated Jun. 13, 2023 from the JPO in a Japanese patent application No. 2020-166470 corresponding to the instant patent application. This office action translation is submitted now in order to supplement the understanding of the cited references which are being disclosed in the instant Information Disclosure Statement.

*Primary Examiner* — Don K Wong
(74) *Attorney, Agent, or Firm* — SOLARIS Intellectual Property Group, PLLC

(57) ABSTRACT

A display device including: a display unit which is provided between a breast and a radiation source of a mammography apparatus that irradiates the breast compressed by a compression member with radiation from the radiation source to capture a radiographic image and displays auxiliary information for assisting a capture of an image of the breast; and a moving mechanism which moves the display unit between a position inside an irradiation field of the radiation and a position outside the irradiation field of the radiation.

13 Claims, 8 Drawing Sheets

(58) Field of Classification Search
CPC .... A61B 2010/009; A61B 2017/22047; A61B 1/0005; A61B 2090/392; G06T 2207/30068
See application file for complete search history.

(56) References Cited

U.S. PATENT DOCUMENTS

| | | |
|---|---|---|
| 2009/0225936 A1 | 9/2009 | Kashiwagi et al. |
| 2009/0232271 A1 | 9/2009 | Sendai |
| 2010/0111250 A1 | 5/2010 | Tsuji et al. |
| 2012/0020454 A1 | 1/2012 | Murakoshi et al. |
| 2017/0000436 A1* | 1/2017 | Shimada ................ A61B 6/502 |
| 2017/0281124 A1 | 10/2017 | Arai et al. |
| 2020/0100760 A1 | 4/2020 | Fukuyo |

FOREIGN PATENT DOCUMENTS

| | | |
|---|---|---|
| JP | 2009-207808 A | 9/2009 |
| JP | 2009-254787 A | 11/2009 |
| JP | 2010-110469 A | 5/2010 |
| JP | 2012-024339 A | 2/2012 |
| JP | 2015-522337 A | 8/2015 |
| JP | 2017-184864 A | 10/2017 |
| JP | 2020-049000 A | 4/2020 |

\* cited by examiner

DISPLAY DEVICE AND CONTROL PROGRAM

CROSS-REFERENCE TO RELATED APPLICATION

The present application claims priority under 35 U.S.C. § 119 to Japanese Patent Application No. 2020-166470 filed on Sep. 30, 2020. The above application is hereby expressly incorporated by reference, in its entirety, into the present application.

BACKGROUND

Technical Field

The present disclosure relates to a display device and a non-transitory computer-readable storage medium storing a control program.

Description of the Related Art

A mammography apparatus is known which irradiates a breast compressed by a compression member with radiation to capture a radiographic image. In a case in which imaging is performed, auxiliary information for assisting the imaging may be displayed. For example, JP2015-522337A discloses a technique in which a display unit, such as an electronic paper or a liquid crystal display (LCD), is provided on a surface of a compression element compressing the breast and auxiliary information, such as a skin line of the breast, is displayed on the electronic paper or the LCD.

However, in a case in which the breast is irradiated with radiation to perform imaging in a state in which the display unit for displaying the auxiliary information is located in the irradiation field of the radiation, the display unit is likely to appear in the captured radiographic image.

The present disclosure has been made in view of the above-mentioned problems, and an object of the present disclosure is to provide a display device and a non-transitory computer-readable storage medium storing a control program that can prevent a display unit from appearing in a radiographic image.

SUMMARY

In order to achieve the above object, according to a first aspect of the present disclosure, there is provided a display device comprising: a display unit which is provided between a breast and a radiation source of a mammography apparatus that irradiates the breast compressed by a compression member with radiation from the radiation source to capture a radiographic image and displays auxiliary information for assisting a capture of an image of the breast; and a moving mechanism which moves the display unit between a position inside an irradiation field of the radiation and a position outside the irradiation field of the radiation.

Further, according to a second aspect of the present disclosure, the display device according to the first aspect may further comprise at least one processor. The processor may direct the moving mechanism to move the display unit to the position outside the irradiation field before the radiation is emitted from the radiation source.

According to a third aspect of the present disclosure, the display device according to the first aspect may further comprise at least one processor. The processor may direct the moving mechanism to move the display unit to the position outside the irradiation field in a case in which the compression of the breast by the compression member is completed.

According to a fourth aspect of the present disclosure, the display device according to the first aspect may further comprise at least one processor. The processor may direct the moving mechanism to move the display unit to the position inside the irradiation field in a case in which the emission of the radiation by the radiation source is stopped.

According to a fifth aspect of the present disclosure, the display device according to the first aspect may further comprise at least one processor. The processor may direct the moving mechanism to locate the display unit at the position outside the irradiation field while the radiation is being emitted from the radiation source.

According to a sixth aspect of the present disclosure, the display device according to the first aspect may further comprise at least one processor. The processor may direct the moving mechanism to locate the display unit at the position inside the irradiation field while the radiation is being emitted from the radiation source.

According to a seventh aspect of the present disclosure, in the display device according to the first aspect, the moving mechanism may rotate and move the display unit between the position inside the irradiation field of the radiation and the position outside the irradiation field of the radiation.

According to an eighth aspect of the present disclosure, in the display device according to the first aspect, the moving mechanism may move the display unit between the position inside the irradiation field of the radiation and the position outside the irradiation field of the radiation in a direction intersecting a direction in which the radiation is emitted.

According to a ninth aspect of the present disclosure, in the display device according to the first aspect, the display unit may be provided in the compression member.

According to a tenth aspect of the present disclosure, in the display device according to the first aspect, the display unit may be provided between the compression member and the radiation source.

According to an eleventh aspect of the present disclosure, in the display device according to the first aspect, the auxiliary information displayed on the display unit may be switched according to at least one of a compression pressure of the compression member against the breast or a height of the compression member.

According to a twelfth aspect of the present disclosure, in the display device according to the first aspect, the auxiliary information may be at least one of information indicating the compression pressure of the compression member against an opposite breast of the same subject with the breast in a case in which an image of the opposite breast is captured by the mammography apparatus, information indicating a thickness of the opposite breast compressed by the compression member, or a radiographic image of the opposite breast.

In addition, in order to achieve the above object, according to a thirteenth aspect of the present disclosure, there is provided a non-transitory computer-readable storage medium storing a control program that causes a computer to execute a process of performing control to move a display unit, which is provided between a breast and a radiation source of a mammography apparatus that irradiates the breast compressed by a compression member with radiation from the radiation source to capture a radiographic image and displays auxiliary information for assisting a capture of an image of the breast, between a position inside an irradiation field of the radiation and a position outside the irradiation field of the radiation.

According to the present disclosure, it is possible to prevent the display unit from appearing in the radiographic image.

BRIEF DESCRIPTION I/F THE DRAWINGS

Exemplary embodiments according to the technique of the present disclosure will be described in detail based on the following figures, wherein.

DETAILED DESCRIPTION

Hereinafter, embodiments of the present disclosure will be described in detail with reference to the drawings. In addition, each of the embodiments does not limit the present disclosure.

Figure 1:
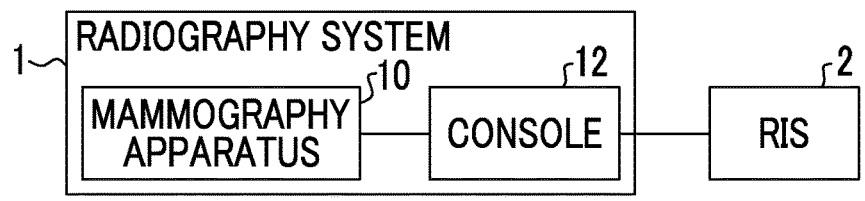
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

Figure 2A:
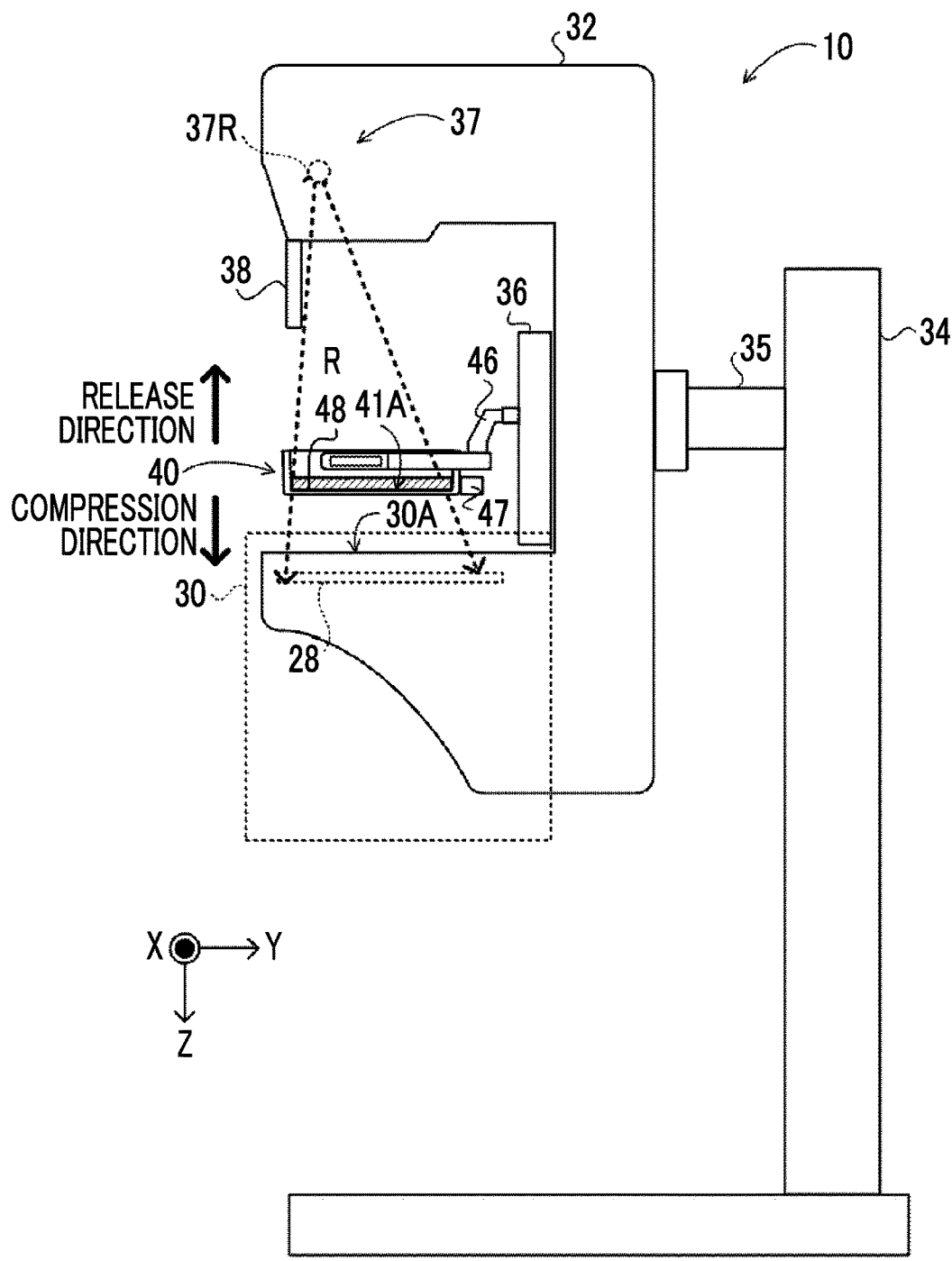
FIG. 2A is a side view illustrating an example of the outward appearance of a mammography apparatus according to the embodiment.
Figure 4:
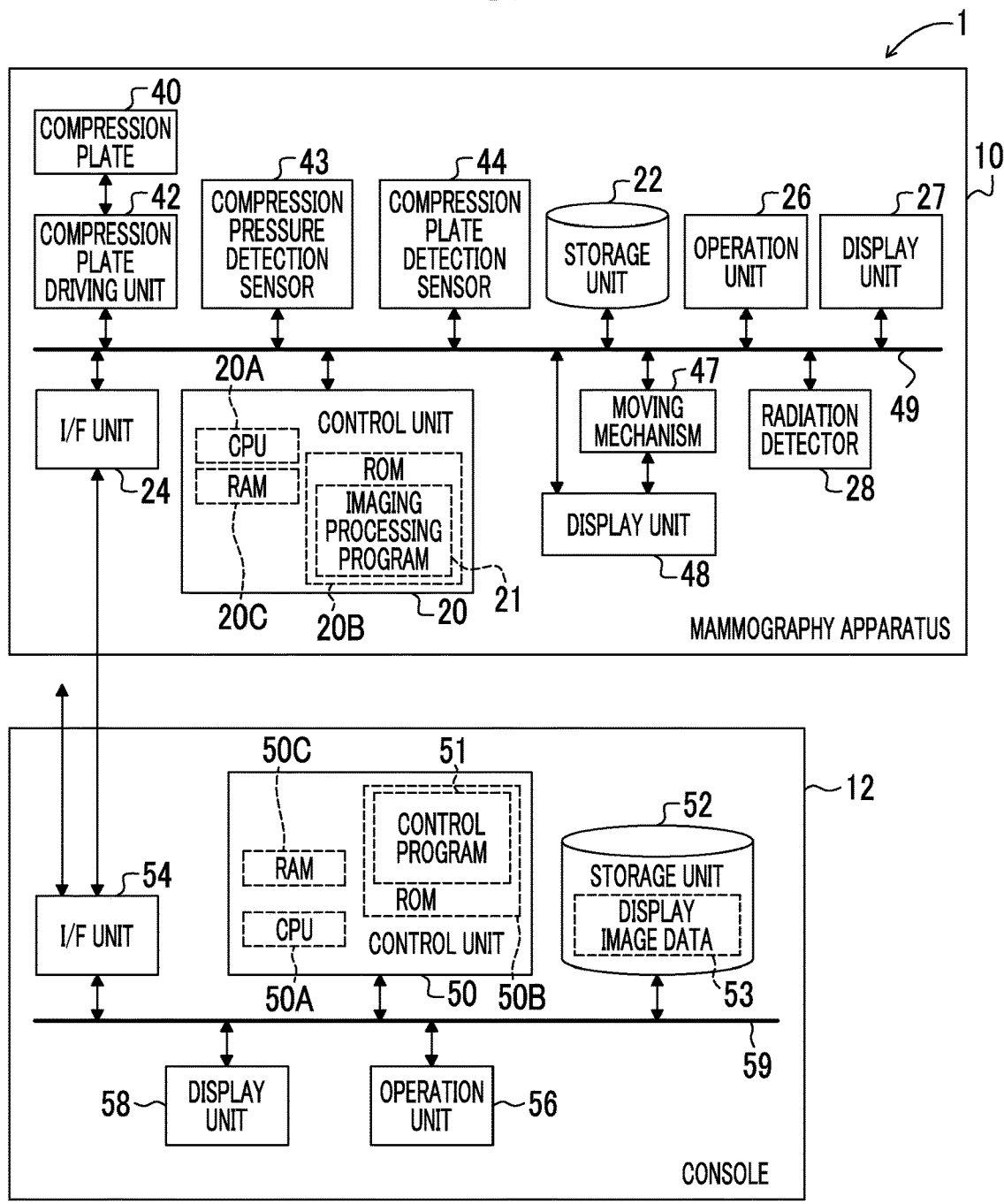
FIG. 4 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 4 is a functional block diagram illustrating an example of the configuration of the mammography apparatus 10 and the console 12 according to this embodiment.

The mammography apparatus 10 according to this embodiment irradiates a breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. The face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 4) that moves a compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. As illustrated in FIG. 2A, for the movement direction of the compression plate 40, the direction in which the breast is compressed, that is, the direction in which the compression plate 40 becomes closer to the imaging surface 30A is referred to as a "compression direction", and the direction in which the compression of the breast is released, that is, the direction in which the compression plate 40 becomes closer to the radiation emitting unit 37 is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression pressure detection sensor (see a compression pressure detection sensor 43 in FIG. 4) and a compression plate detection sensor (see a compression plate detection sensor 44 in FIG. 4). The compression pressure detection sensor 43 detects compression pressure which is pressure related to the compression plate 40. Examples of the compression pressure detection sensor include a semiconductor-type pressure sensor, a capacitance-type pressure sensor, and a strain gauge such as a load cell. Further, the compression force of the compression plate 40 against the entire breast or compression pressure which is compression force per unit area may be applied as the compression pressure. In addition, the compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2B:
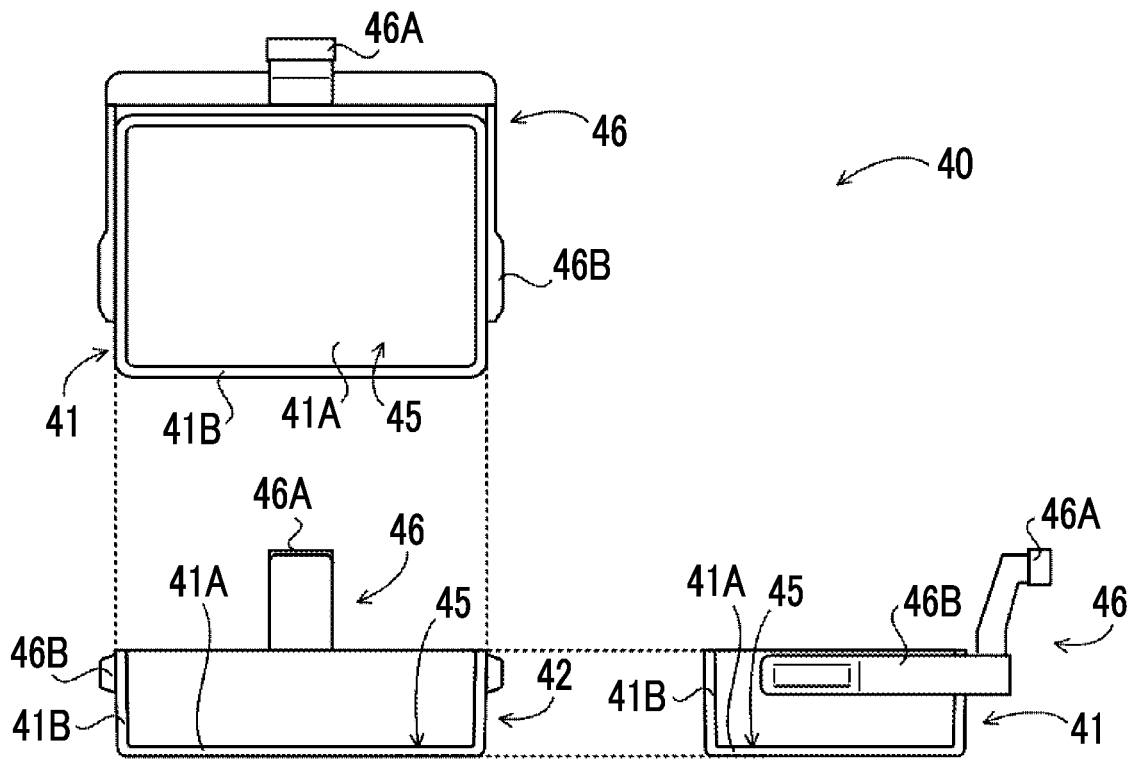
FIG. 2B is a three-view diagram illustrating an example of a compression plate according to the embodiment.

As a specific example, the compression plate 40 that can be attached to the mammography apparatus 10 according to this embodiment will be described with reference to FIG. 2B. FIG. 2B is a three-view diagram illustrating an example of the compression plate 40 according to this embodiment. The three-view diagram illustrated in FIG. 2B includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2B, the compression plate 40 according to this embodiment includes a compression portion 41 and a support portion 46.

It is preferable that the compression plate 40 is optically transparent in order to check positioning or a compressed state. In addition, the compression plate 40 is made of a material having high transmittance for the radiation R.

The support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

On the other hand, the compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height.

The bottom portion 41A is provided with a display unit 48 that displays auxiliary information assisting the capture of the image of the breast. Examples of the display unit 48 include a liquid crystal display (LCD) and an electronic paper. In addition, the display unit 48 may be provided in the entire bottom portion 41A of the compression plate 40 or may be provided in a partial region of the bottom portion 41A. The region in which the display unit 48 is provided can be determined according to the range in which the auxiliary information is displayed.

Figure 3A:
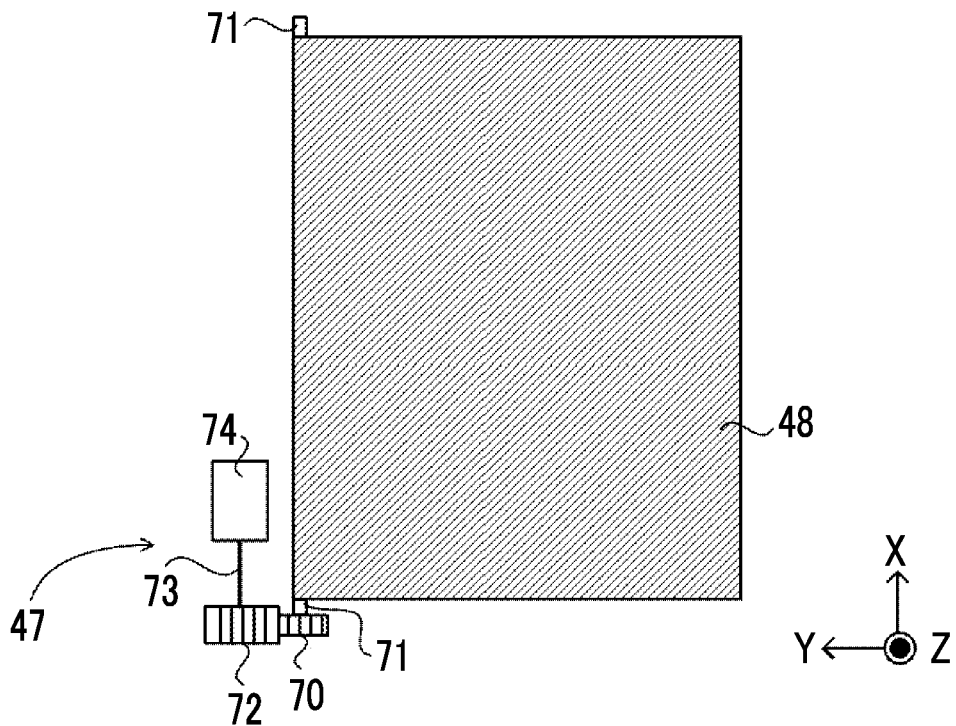
FIG. 3A is a plan view illustrating an example of a moving mechanism and a display unit as viewed from a radiation source.
Figure 3B:
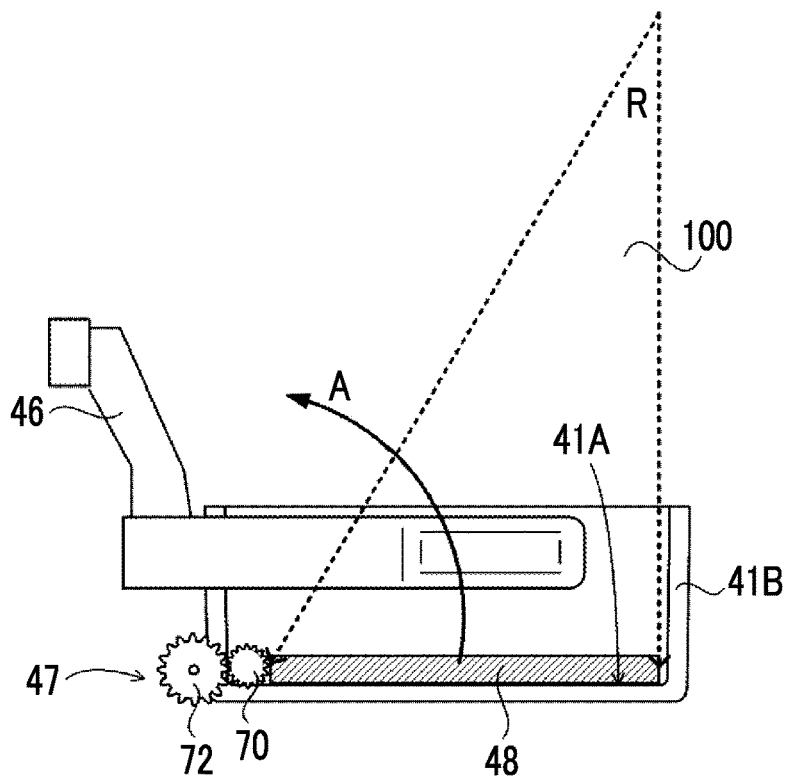
FIG. 3B is a side view illustrating an example of a state in which the moving mechanism moves the display unit into an irradiation field.

The display unit 48 is moved between a position inside the irradiation field of the radiation R and a position outside the irradiation field by a moving mechanism 47. FIG. 3A is a plan view illustrating an example of the moving mechanism 47 and the display unit 48 as viewed from the radiation source 37R. Further, FIG. 3B is a side view illustrating an example of a state in which the display unit 48 is moved into an irradiation field 100 by the moving mechanism 47. Furthermore, FIG. 3C is a side view illustrating an example of a state in which the display unit 48 is moved out of the irradiation field 100 by the moving mechanism 47.

Figure 3C:
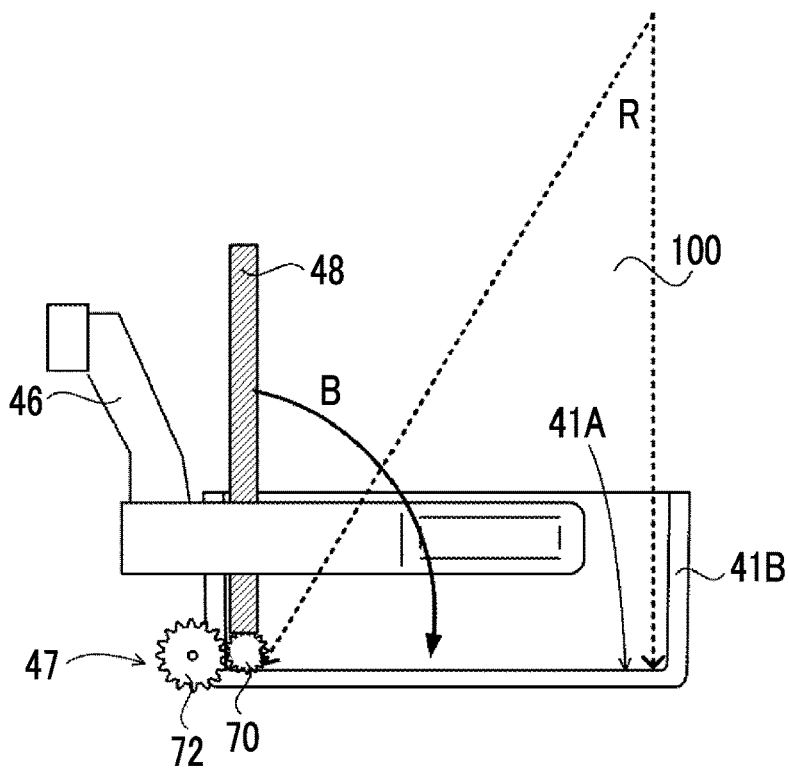
FIG. 3C is a side view illustrating an example of a state in which the moving mechanism moves the display unit out of the irradiation field.

As illustrated in FIGS. 3A to 3C, the moving mechanism 47 according to this embodiment includes a gear 70, an axle 71, a gear 72, a shaft 73, and a motor 74. The axle 71 of the gear 70 is provided at a position near the bottom portion 41A on the chest wall side so as to penetrate the side wall portion 41B of the compression plate 40 in the left-right direction of the subject. The axle 71 can be rotated by the rotation of the gear 70. A side surface of the display unit 48 is attached to the axle 71, and the display unit 48 is rotated with the rotation of the axle 71.

In addition, the gear 72 that has a shaft of the motor 74 as an axle is disposed so as to be engaged with the gear 70. In a case in which the motor 74 is driven, the power of the shaft 73 is transmitted to rotate the gear 72 and the gear 70. The display unit 48 attached to the axle 71 is rotated and moved between the position inside the irradiation field 100 and the position outside the irradiation field 100 with the rotation of the gear 70. As illustrated in FIG. 3B, in a case in which the display unit 48 is located inside the irradiation field 100 and the motor 74 is driven, the gear 70 and the gear 72 are rotated, and the display unit 48 is rotated in the direction of an arrow A to move to the position outside the irradiation field 100 and is in the state illustrated in FIG. 3C. On the other hand, as illustrated in FIG. 3C, in a case in which the display unit 48 is located outside the irradiation field 100 and the motor 74 is driven, the gear 70 and the gear 72 are rotated, and the display unit 48 is rotated in the direction of an arrow B to move to the position inside the irradiation field 100 and is in the state illustrated in FIG. 3B.

The motor 74 of the moving mechanism 47 and the display unit 48 are electrically connected to a control unit 20 in the imaging table 30 through the support portion 46, and the driving thereof is controlled by the control unit 20. In addition, each of the motor 74 and the display unit 48 may be electrically connected to the control unit 20 of the mammography apparatus 10 without passing through the support portion 46 or may be electrically connected to the control unit 20 by, for example, wireless communication. The control unit 20 drives the moving mechanism 47 and the display unit 48 under the control of the control unit 50 of the console 12. The control unit 20, the moving mechanism 47, the display unit 48, and the control unit 50 according to this embodiment are an example of a display device according to the present disclosure.

Furthermore, the control unit 20, a storage unit 22, an interface (I/F) unit 24, an operation unit 26, and a display unit 27 illustrated in FIG. 4 are provided in the imaging table 30 of the mammography apparatus 10 according to this embodiment. The control unit 20, the storage unit 22, the I/F unit 24, the operation unit 26, the display unit 27, the radiation detector 28, the compression plate driving unit 42, the compression pressure detection sensor 43, the compression plate detection sensor 44, the moving mechanism 47, and the display unit 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 4, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a control program 51 (which will be described below) executed by the CPU 50A are stored in the ROM 50B in advance. The RAM 50C temporarily stores various kinds of data. The CPU 50A according to this embodiment is an example of a processor according to the present disclosure. The control program 51 according to this embodiment is an example of a control program according to the present disclosure.

The storage unit 52 stores, for example, display image data 53, the image data of the radiographic image captured by the mammography apparatus 10, and various other kinds of information. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 5:
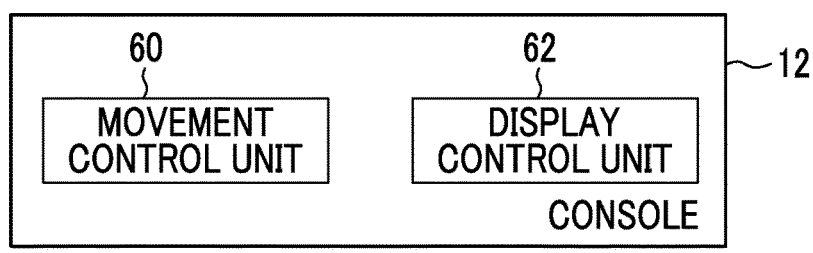
FIG. 5 is a functional block diagram illustrating an example of the function of the console according to the embodiment.

In addition, FIG. 5 is a functional block diagram illustrating an example of the configuration of the console 12 according to this embodiment. As illustrated in FIG. 5, the console 12 comprises a movement control unit 60 and a display control unit 62. For example, in the console 12 according to this embodiment, the CPU 50A of the control unit 50 executes the control program 51 stored in the ROM 50B to function as the movement control unit 60 and the display control unit 62.

The movement control unit 60 has a function of driving the moving mechanism 47 to move the display unit 48 between the position inside the irradiation field 100 and the position outside the irradiation field 100 as described above. For example, in a case in which the radiation source 37R does not emit radiation in the mammography apparatus 10, the movement control unit 60 according to this embodiment locates the display unit 48 at the position inside the irradiation field 100 as illustrated in FIG. 3B. Therefore, in a case in which the user positions the breast, the display unit 48 is disposed along the bottom portion 41A of the compression portion 41 of the compression plate 40 as illustrated in FIG. 3B. Therefore, in a case in which auxiliary information is displayed on the display unit 48, this is equivalent to a state in which the auxiliary information is displayed on the bottom portion 41A of the compression plate 40.

In addition, in a case in which the radiation source 37R emits radiation in the mammography apparatus 10, the movement control unit 60 according to this embodiment locates the display unit 48 at the position outside the irradiation field 100 as illustrated in FIG. 3C. Therefore, while the radiographic image of the breast is being captured, specifically, while the radiation detector 28 is being irradiated with the radiation R transmitted through the breast, the display unit 48 is disposed along the wall portion 41B on the chest wall side in the compression portion 41 of the compression plate 40 as illustrated in FIG. 3C. Therefore, the display unit 48 does not appear in the radiographic image captured by the radiation detector 28.

The display control unit 62 has a function of displaying the auxiliary information on the display unit 48. In this embodiment, a skin line indicating the shape of the breast compressed by the compression plate 40 and the current compression pressure of the compression plate 40 against the breast are used as the auxiliary information.

Specifically, the display control unit 62 acquires the display image data 53 corresponding to the compression plate identifier of the compression plate 40 attached to the mammography apparatus 10 from the storage unit 52. The display image data 53 is image data of an image indicating the skin line of the breast in a case in which a standard breast is compressed into an ideal state. In some cases, the size of the compression portion 41 and the size of the bottom portion 41A vary depending on the type of the compression plate 40. Therefore, in some cases, the size of the display unit 48, that is, auxiliary information display image data for displaying auxiliary information varies depending on the type of the compression plate 40. Therefore, in this embodiment, a plurality of display image data items 53 corresponding to the types of the compression plates 40 are stored in the storage unit 52 so as to be associated with the compression plate identifiers. The display control unit 62 acquires the display image data 53 corresponding to the compression plate identifier input from the mammography apparatus 10 from the storage unit 52 and outputs the display image data 53 to the mammography apparatus 10 through the I/F unit 54.

In addition, the display control unit 62 according to this embodiment has a function of ending the display of the auxiliary information on the display unit 48 in a case in which the display unit 48 is moved from the position inside the irradiation field 100 to the position outside the irradiation field 100. Specifically, in a case in which the movement control unit 60 moves the display unit 48 from the position inside the irradiation field 100 to the position outside the irradiation field 100, the display control unit 62 outputs an end control signal for ending the display of the auxiliary information by the display unit 48 to the mammography apparatus 10 through the I/F unit 54.

Figure 6:
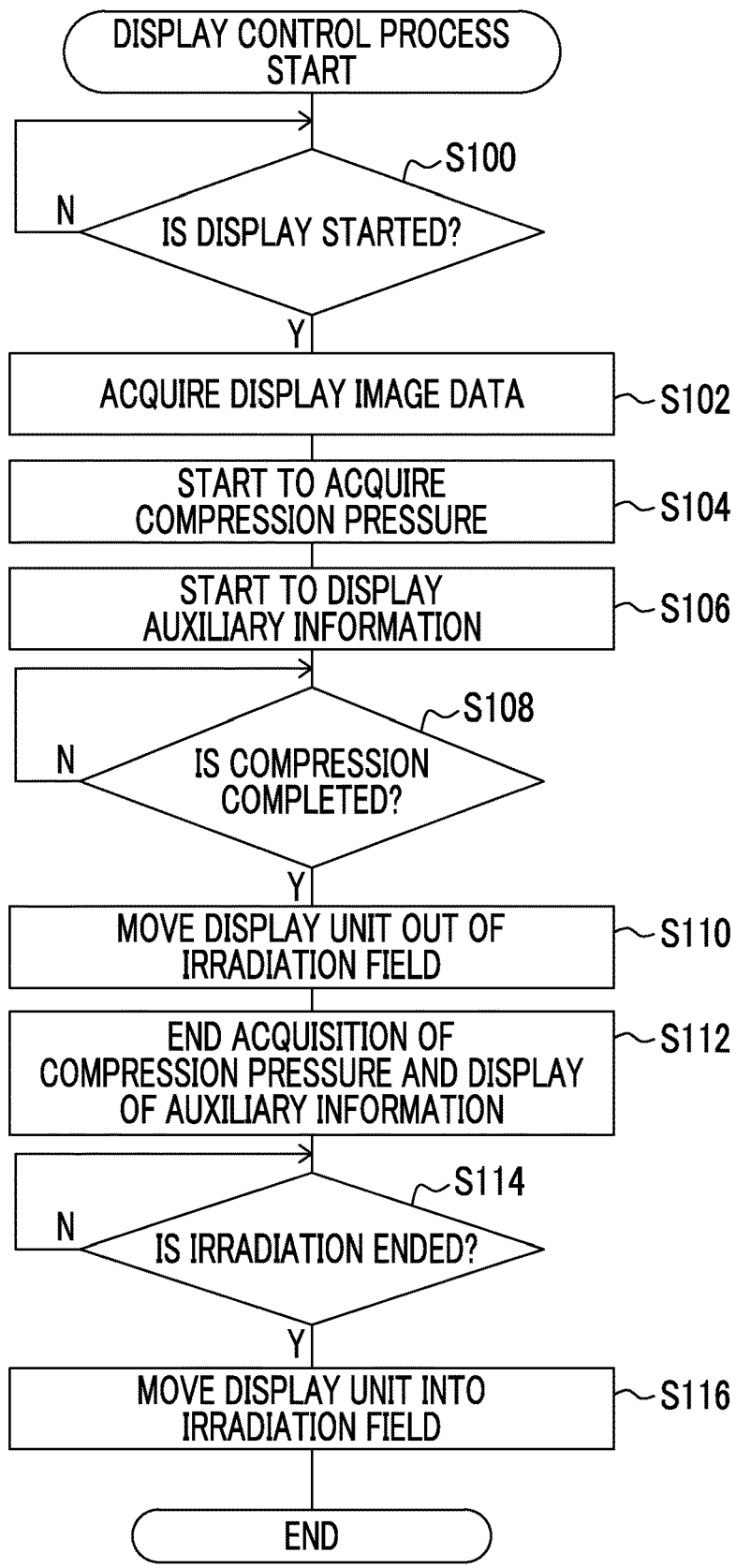
FIG. 6 is a flowchart illustrating an example of the flow of a display control process according to the embodiment.

Next, the operation of the console 12 in the display of the auxiliary information by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, it performs a display control process illustrated in FIG. 6. In the console 12 according to this embodiment, for example, the CPU 50A of the control unit 50 executes the control program 51 stored in the ROM 50B to perform the display control process whose example is illustrated in FIG. 6. FIG. 6 is a flowchart illustrating an example of the flow of the display control process performed in the console 12 according to this embodiment. In addition, in an initial state, the display unit 48 is disposed inside the irradiation field 100 as illustrated in FIG. 3B.

In Step S100 of FIG. 6, the display control unit 62 determines whether or not to start the display of the auxiliary information. In a case in which the user wants to start the display of the auxiliary information, the user instructs the start of the display with the operation unit 26 of the mammography apparatus 10. The mammography apparatus 10 outputs a display start instruction signal through the I/F unit 24. In a case in which the display start instruction signal is input to the console 12, the display control unit 62 starts to display the auxiliary information. Therefore, the determination result in Step S100 is "No" until the display start instruction signal is input to the console 12. On the other hand, in a case in which the display start instruction signal is input to the console 12, the determination result in Step S100 is "Yes", and the process proceeds to Step S102.

In Step S102, the display control unit 62 acquires the compression plate identifier from the mammography apparatus 10 and acquires the display image data 53 corresponding to the acquired compression plate identifier from the storage unit 52 as described above.

Then, in Step S104, the display control unit 62 starts to acquire compression pressure. Specifically, the display control unit 62 acquires the compression pressure detected by the compression pressure detection sensor 43 of the mammography apparatus 10 through the I/F unit 24 and the I/F unit 54.

That is, the display control unit 62 starts to acquire the current compression pressure related to the compression plate 40.

Figure 7:
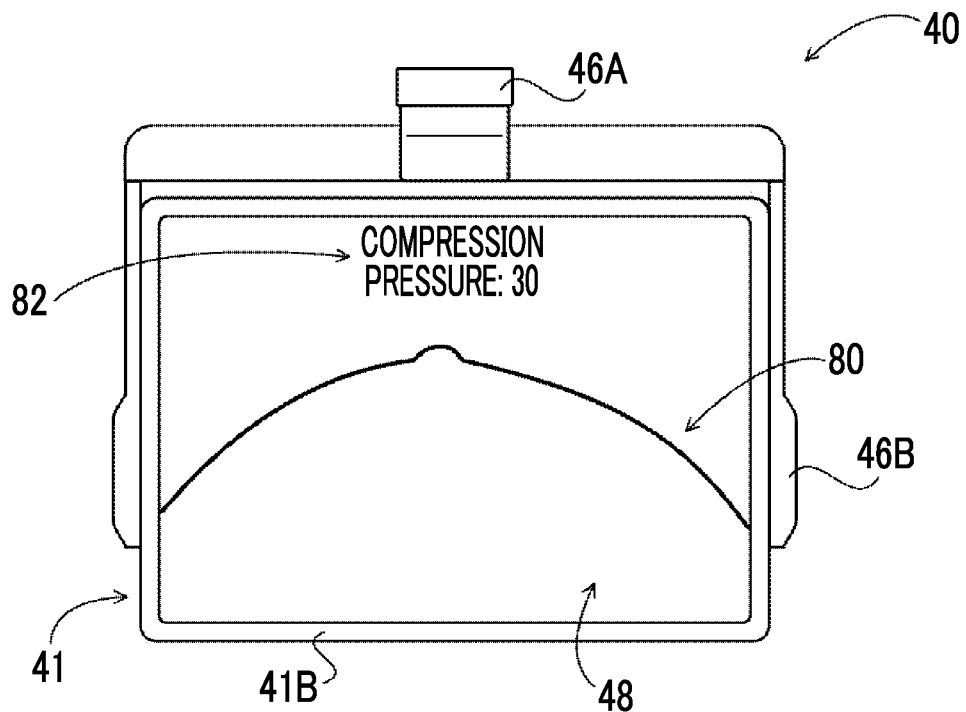
FIG. 7 is a diagram illustrating an example of auxiliary information displayed on the display unit.

Then, in Step S106, the display control unit 62 starts the display of the auxiliary information by the display unit 48. Specifically, the display control unit 62 generates auxiliary information display image data indicating an image obtained by combining the auxiliary information which is the skin line indicated by the display image data 53 acquired in Step S102 and the auxiliary information indicating the compression pressure started to be acquired in Step S104. Then, the display control unit 62 outputs the generated auxiliary information display image data to the mammography apparatus 10 through the I/F unit 54. In the mammography apparatus 10, in a case in which the auxiliary information display image data is input, the control unit 20 performs control to direct the display unit 48 to display the auxiliary information corresponding to the auxiliary information display image data. An image corresponding to the auxiliary information is displayed on the display unit 48 provided in the compression plate 40 of the mammography apparatus 10 by this control. In this embodiment, as described above, an image indicating the skin line of the breast and the compression pressure is displayed on the display unit 48. FIG. 7 illustrates an example of a skin line 80 and compression pressure 82 displayed on the display unit 48. The user compresses the breast of the subject positioned with reference to the displayed skin line 80 and compression pressure 82 with the compression plate 40.

Then, in Step S108, the movement control unit 60 determines whether or not the compression of the breast by the compression plate 40 is completed. For example, the movement control unit 60 according to this embodiment determines whether or not the compression of the breast is completed on the basis of the compression pressure detected by the compression pressure detection sensor 43. In a case in which the compression of the breast is completed, the user stops the movement of the compression plate 40. The compression pressure applied to the compression plate 40 gradually increases until compression is completed after the compression plate 40 comes into contact with the breast. However, in a case in which the movement of the compression plate 40 is stopped, the compression pressure related to the compression plate 40 hardly changes. For this reason, in this embodiment, a case in which the compression pressure of the compression plate 40 against the breast does not change for a predetermined time or longer is regarded as the case in which the compression of the breast is completed. Therefore, in a case in which the compression pressure detected by the compression pressure detection sensor 43 does not change for a predetermined time or longer, the movement control unit 60 determines that the compression of the breast by the compression plate 40 is completed. Further, in this embodiment, the detection that the compression pressure does not change is not limited to a case in which the compression pressure does not change at all, and a change in the compression pressure which is regarded as an error is ignored. Furthermore, the predetermined time is not particularly limited. For example, in this embodiment, the predetermined time is a time that is at least longer than the time until the compression plate 40 is moved from an initial position of the compression plate 40 to a position where it comes into contact with the breast having a standard thickness. Examples of the initial position of the compression plate 40 include a position that is closest to the radiation source 37R among the positions of the compression plate 40 attached to the compression unit 36 of the mammography apparatus 10.

The determination result in step S108 is "No" until the compression of the breast is completed. In addition, in this case, the display control unit 62 acquires the compression pressure detected by the compression pressure detection sensor 43 from the mammography apparatus 10 at a predetermined timing, generates auxiliary information display image data obtained by updating the auxiliary information indicating the current compression pressure, and sequentially outputs the auxiliary information display image data to the mammography apparatus 10. In a case in which the auxiliary information display image data is input from the console 12, the mammography apparatus 10 sequentially updates the auxiliary information display image data displayed on the display unit 48. Then, the current compression pressure 82 is displayed as the auxiliary information on the display unit 48.

On the other hand, in a case in which the compression of the breast is completed in Step S108, the determination result is "Yes", and the process proceeds to Step S110. In Step S110, the movement control unit 60 moves the display unit 48 out of the irradiation field 100 as described above. Specifically, the movement control unit 60 drives the motor 74 of the moving mechanism 47 to rotate the gear 70 and the gear 72 under the control of the control unit 20 of the mammography apparatus 10 such that the display unit 48 is rotated and moved from the position inside the irradiation field 100 illustrated in FIG. 3B to the position outside the irradiation field 100 illustrated in FIG. 3C.

Then, in Step S112, the display control unit 62 ends the acquisition of the compression pressure started in Step S104. In addition, the display control unit 62 ends the display of the auxiliary information started in Step S106. Specifically, as described above, the display control unit 62 outputs the end control signal for ending the display of the auxiliary information by the display unit 48 to the mammography apparatus 10 through the I/F unit 54. In the mammography apparatus 10, in a case in which the end control signal is input from the console 12, the control unit 20 ends the display of the auxiliary information corresponding to the auxiliary information display image data by the display unit 48.

In a case in which the compression of the breast is completed, the user instructs the emission of the radiation R. In a case in which the mammography apparatus 10 receives an instruction to emit the radiation R, the radiation R is emitted from the radiation source 37R of the radiation emitting unit 37, and the radiation detector 28 captures a radiographic image of the breast. In addition, in the mammography apparatus 10 according to this embodiment, the radiation source 37R emits the radiation R only while the user instructs the emission of the radiation R, specifically, only while the user presses an irradiation button included in the operation unit 56. In a case in which the user releases the irradiation button, the emission of the radiation R ends.

Then, in Step S114, the movement control unit 60 determines whether or not the emission of the radiation R ends. In this embodiment, it is determined whether or not the user's instruction to emit the radiation R is continued as described above. In a case in which the user's instruction to emit the radiation R is continued, the determination result in Step S114 is "No" since the emission of the radiation R has not ended yet. On the other hand, in a case in which the user's instruction to emit the radiation R ends, the determination result in Step S114 is "Yes" since the emission of the radiation R ends, and the process proceeds to Step S116. In addition, a method for determining whether or not the emission of the radiation R ends in the movement control unit 60 is not limited to this aspect. For example, in a case in which the image data of the captured radiographic image of the breast is output from the radiation detector 28, the movement control unit 60 may determine that the emission of the radiation R ends.

In Step S116, the movement control unit 60 moves the display unit 48 into the irradiation field 100 as described above. Specifically, the movement control unit 60 drives the motor 74 of the moving mechanism 47 to rotate the gear 70 and the gear 72 under the control of the control unit 20 of the mammography apparatus 10 such that the display unit 48 is rotated and moved from the position outside the irradiation field 100 illustrated in FIG. 3C to the position inside the irradiation field 100 illustrated in FIG. 3B. In a case in which the process in Step S116 ends, the display control process illustrated in FIG. 6 ends.

In addition, how the moving mechanism 47 moves the display unit 48 between the position inside the irradiation field 100 and the position outside the irradiation field 102 and a specific configuration of the moving mechanism 47 are not limited to the above-mentioned aspect. For example, the following modification examples may be used.

Modification Examples

In the above-described embodiment, the aspect in which the display unit 48 is rotated and moved between the position inside the irradiation field 100 and the position outside the irradiation field 102 as illustrated in FIGS. 3A to 3C has been described. In contrast to this, in this modification example, an aspect will be described in which a moving mechanism 47 illustrated in FIGS. 8A to 8C moves the display unit 48 between the position inside the irradiation field 100 and the position outside the irradiation field 100 in a direction intersecting the direction in which the radiation R is emitted. In addition, the direction intersecting the direction in which the radiation R is emitted is, for example, the in-plane direction of the imaging surface 30A of the imaging table 30 and is the XY direction in FIGS. 2A and 8A.

Figure 8A:
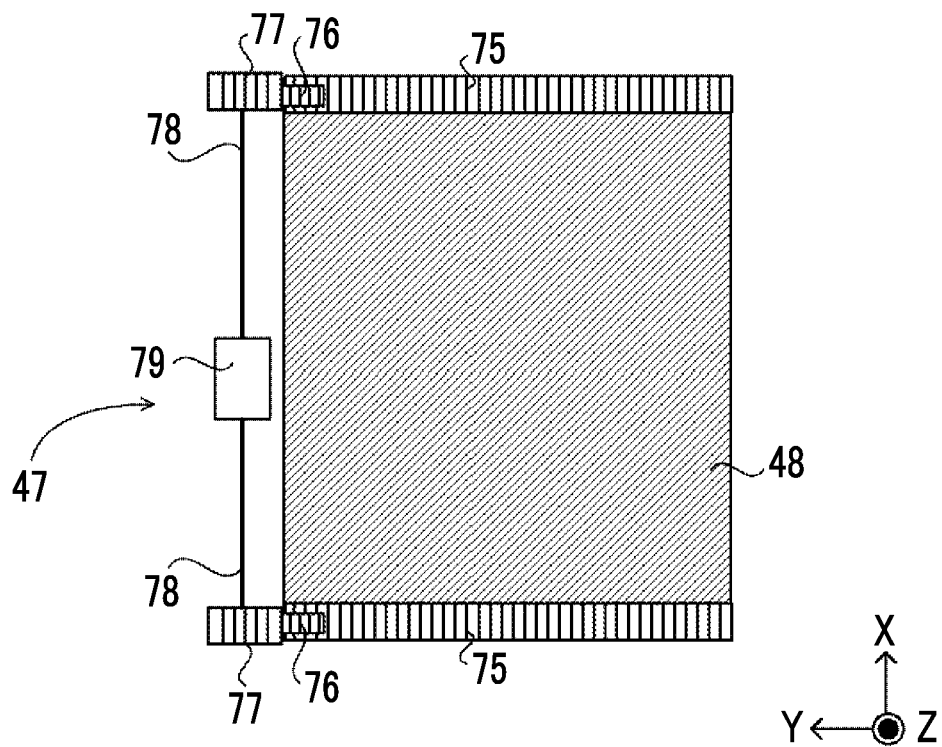
FIG. 8A is a plan view illustrating a modification example of the moving mechanism and the display unit as viewed from the radiation source.
Figure 8B:
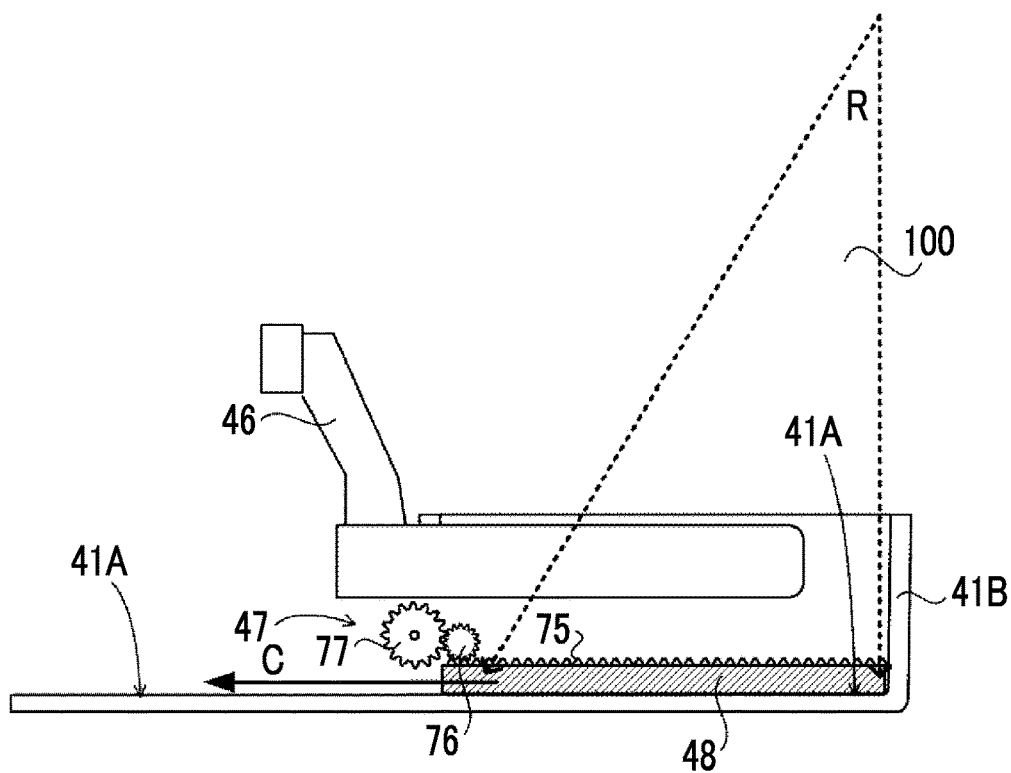
FIG. 8B is a side view illustrating a modification example of a state in which the moving mechanism moves the display unit into the irradiation field.
Figure 8C:
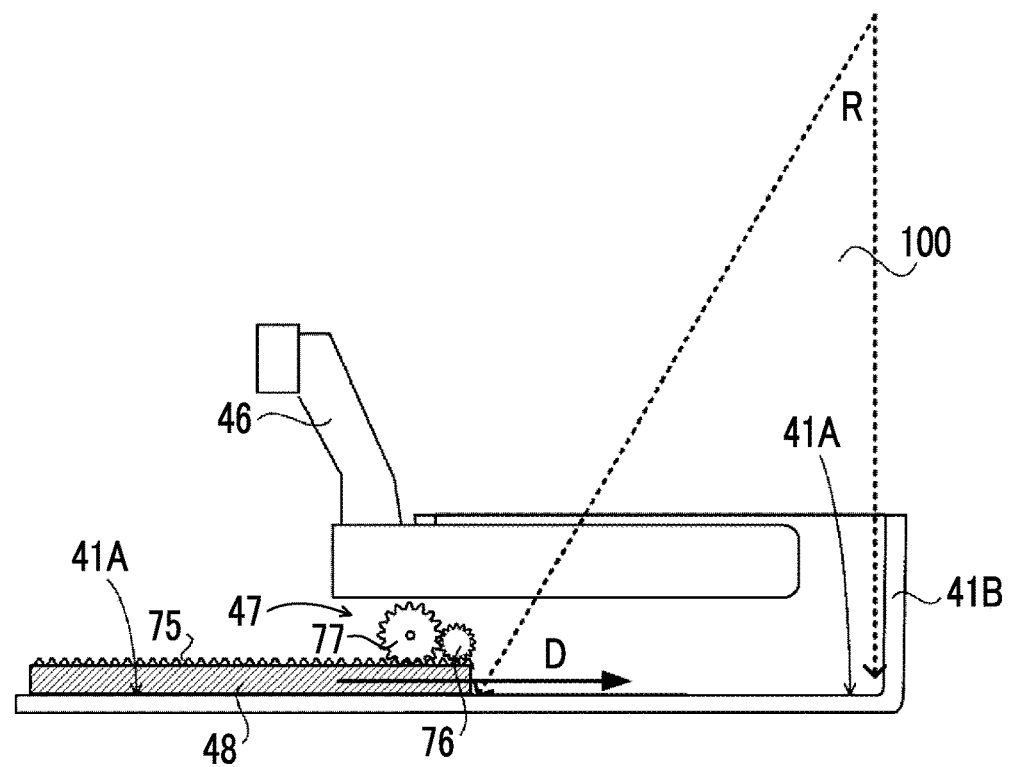
FIG. 8C is a side view illustrating a modification example of a state in which the moving mechanism moves the display unit out of the irradiation field.

FIG. 8A is a plan view illustrating an example of the moving mechanism 47 and the display unit 48 as viewed from the radiation source 37R. Further, FIG. 8B is a side view illustrating an example of a state in which the moving mechanism 47 moves the display unit 48 into the irradiation field 100. FIG. 8C is a side view illustrating an example of a state in which the moving mechanism 47 moves the display unit 48 out of the irradiation field 100.

As illustrated in FIGS. 8A to 8C, the moving mechanism 47 according to this modification example includes gears 75, gears 76, gears 77, a shaft 78, and a motor 79. The gears 75 are provided on a pair of opposite sides, which corresponds to the left and right sides of the subject, in a surface of the display unit 48 which faces the radiation source 37R. The gear 76 is disposed so as to be engaged with the gear 75 and the gear 77. The gear 77 has a shaft of the motor 79 as an axle. Similarly to the motor 74, the motor 79 is electrically connected to the control unit 20 in the imaging table 30 through the support portion 46, and the driving thereof is controlled by the control unit 20. In a case in which the motor 79 is driven, the power of the shaft 78 is transmitted to the gear 75 through the gear 77 and the gear 76. The display unit 48 slides between the position inside the irradiation field 100 and the position outside the irradiation field 100 with the rotation of the gear 76 and the gear 77. In addition, as illustrated in FIGS. 8B and 8C, in this embodiment, a position away from the chest wall is applied as the position outside the irradiation field 100. Therefore, the moving mechanism 47 moves the display unit 48 between a position on the chest wall side and the position away from the chest wall in the front-rear direction of the subject.

As illustrated in FIG. 8B, in a case in which the display unit 48 is located at the position inside the irradiation field 100 and the motor 79 is driven, the gear 76 and the gear 77 are rotated, and the display unit 48 slides in the direction of an arrow C to move to the position outside the irradiation field 100 and is in the state illustrated in FIG. 8C. On the other hand, as illustrated in FIG. 8C, in a case in which the display unit 48 is located at the position outside the irradiation field 100 and the motor 79 is driven, the gear 76 and the gear 77 are rotated, and the display unit 48 slides in the direction of an arrow D to move to the position inside the irradiation field 100 and is in the state illustrated in FIG. 8B.

In this modification example, since the display unit 48 slides to the position away from the chest wall in this way, an opening portion through which the display unit 48 passes is provided in a portion, which is close to the bottom portion 41A, in the wall portion 41B of the compression plate 40 that is opposite to the chest wall. In addition, the bottom portion 41A extends in a direction in which it becomes further away from the chest wall as illustrated in FIGS. 8B and 8C in order to support the moved display unit 48.

Further, in the aspect illustrated in FIGS. 8A to 8C, the display unit 48 slides in the front-rear direction of the subject. However, the display unit 48 may slide in the left-right direction of the subject.

As described above, the above-described embodiment includes, as the display device, the display unit 48 that is provided between the breast and the radiation source 37R of the mammography apparatus 10 which irradiates the breast compressed by the compression plate 40 with the radiation R from the radiation source 37R to capture a radiographic image and displays the auxiliary information for assisting the capture of the image of the breast and the moving mechanism 47 that moves the display unit 48 between the position inside the irradiation field 100 of the radiation R and the position outside the irradiation field 100 of the radiation R.

As described above, according to the above-described embodiment, the moving mechanism 47 can move the display unit 48 between the position inside the irradiation field 100 of the radiation R and the position outside the irradiation field 100 of the radiation R. Therefore, while the radiation R is emitted to capture a radiographic image, the moving mechanism 47 can locate the display unit 48 at the position outside the irradiation field 100. As a result, according to the above-described embodiment, it is possible to prevent the display unit 48 from appearing in the radiographic image.

In addition, according to the above-described embodiment, the CPU 50A automatically moves the display unit 48 to the position outside the irradiation field 100 after the positioning of the breast is completed. Therefore, since the user does not need to move the display unit 48, it is possible to reduce the burden on the user.

Figure 9:
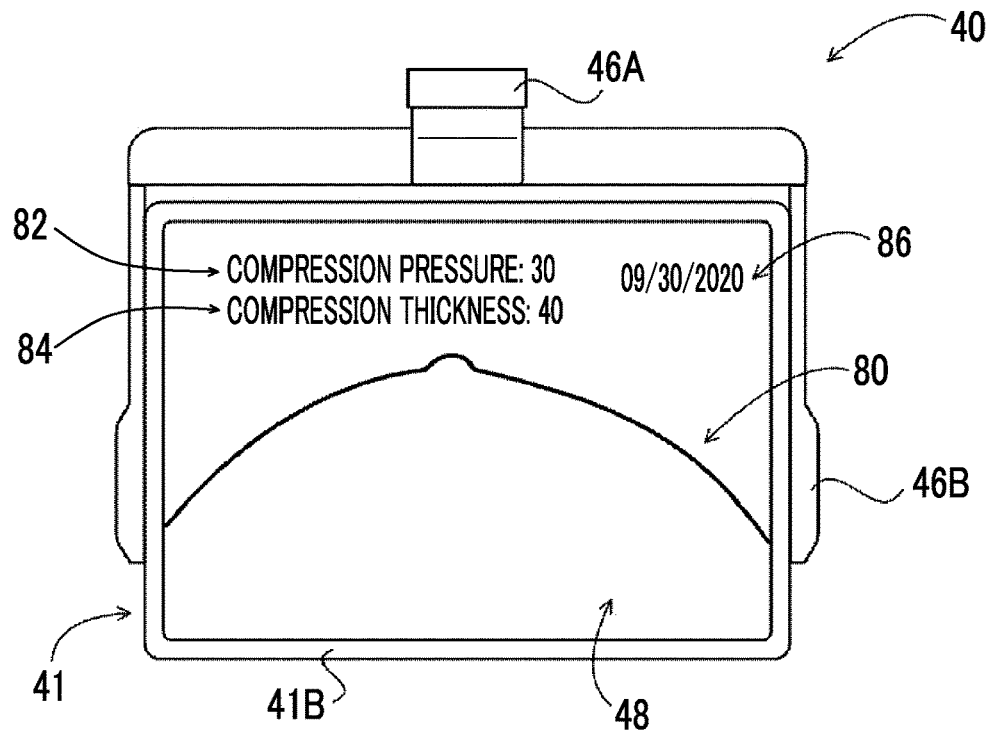
FIG. 9 is a diagram illustrating another example of the auxiliary information displayed on the display unit.

Further, in the above-described embodiment, the aspect in which the skin line 80 indicating the shape of the breast and the compression pressure 82 applied to the compression plate 40 are applied as the auxiliary information has been described. However, the auxiliary information is not limited thereto. For example, as illustrated in FIG. 9, a compression thickness 84 which is the height of the compression plate 40 may be applied as the auxiliary information. In addition, the compression thickness corresponds to the thickness of the compression plate 40 from the imaging surface 30A of the imaging table 30 and corresponds to the thickness of the breast compressed by the compression plate 40. A method for acquiring the compression thickness in the display control unit 62 is not limited. For example, the amount of movement of the compression plate 40 by the compression plate driving unit 42 may be acquired, and the display control unit 62 may acquire the distance between the compression plate 40 and the imaging surface 30A of the imaging table 30 as the compression thickness on the basis of the amount of movement of the compression plate 40. In addition, the compression pressure 82 and the compression thickness 84 may be the compression pressure 82 and the compression thickness 84 in the state in which compression was completed in a case in which the radiographic image of the breast was captured in the past.

Further, for example, as illustrated in FIG. 9, date and time information 86 indicating the imaging date and time may be applied as the auxiliary information. Furthermore, the auxiliary information may be information related to the subject, such as the name of the subject, information related to the radiographer, or the like. Moreover, the auxiliary information indicating the shape of the breast is not limited to the skin line. For example, information indicating the position of the nipple may be applied as the auxiliary information. In addition, the auxiliary information may be the radiographic image of the breast.

Further, in the above-described embodiment, the skin line of the breast in a case in which the standard breast is compressed into an ideal state is applied as the skin line. However, the skin line is not limited to this aspect. For example, an image indicating the skin line generated from the radiographic image of the breast of the same subject captured in the past may be used. In addition, a method for generating the image indicating the skin line is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line.

In addition, the auxiliary information may be at least one of information indicating the compression pressure of the compression plate 40 against the opposite breast of the same subject in a case in which the image of the opposite breast is captured, information indicating the compression thickness of the opposite breast compressed by the compression plate 40, or the radiographic image of the opposite breast. Since the subject is the same, it is possible to use, as reference values, the compression pressure and the compression thickness in the capture of the image of the opposite breast. In addition, the radiographic image of the opposite breast or the skin line generated from the radiographic image of the opposite breast can be reversed in the left-right direction and can be applied as the radiographic image or the skin line of the breast on the side which is captured this time in a pseudo manner.

Further, in the above-described embodiment, the aspect in which the type of the auxiliary information displayed on the display unit 48 is always the same has been described. However, the type of the auxiliary information displayed on the display unit 48 may be switched depending on predetermined conditions. For example, until the compression plate 40 comes into contact with the breast, the name of the subject may be displayed as the auxiliary information. In a case in which the compression plate 40 comes into contact with the breast, the auxiliary information to be displayed may be switched from the name of the subject to the compression pressure or the compression thickness.

Furthermore, in the above-described embodiment, the aspect in which the compression plate 40 is moved to the position outside the irradiation field 100 in a case in which the compression of the breast is completed has been described. However, the timing when the display unit 48 is moved out of the irradiation field 100 is not limited to this aspect. For example, in a case in which the user instructs the emission of the radiation R, the movement control unit 60 may move the display unit 48 out of the irradiation field 100 and then direct the radiation source 37R to emit the radiation R. That is, in a case in which the display unit 48 is located in the irradiation field 100, the movement control unit 60 may perform control to prohibit the emission of the radiation R.

Figure 10:
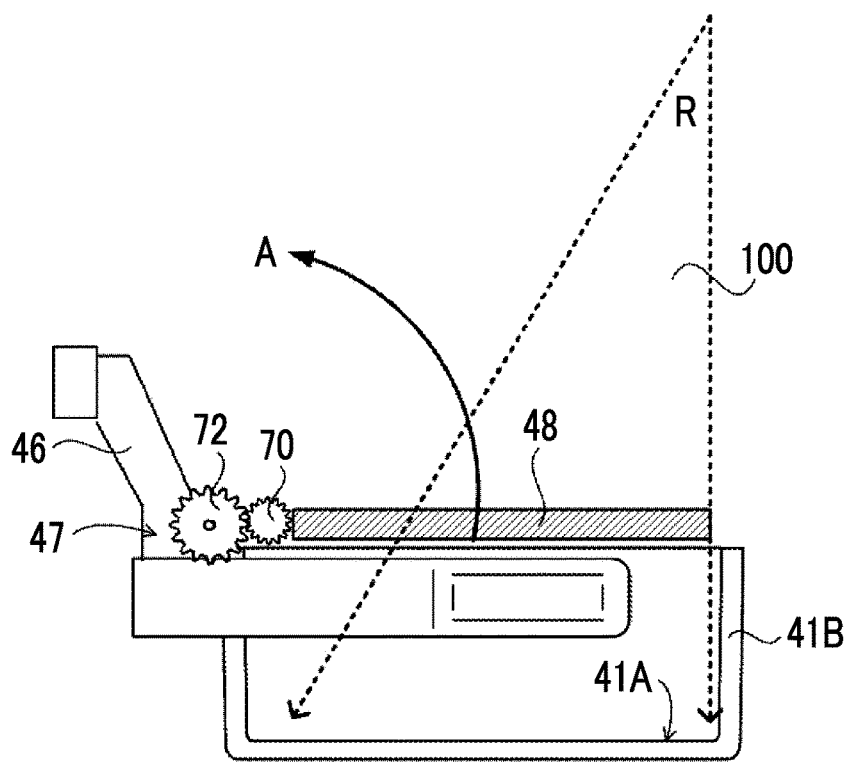
FIG. 10 is a diagram illustrating another example of the position where the display unit is provided.

Further, in the above-described embodiment, the aspect in which the compression plate 40 comprises the display unit 48 has been described. However, the position where the display unit 48 is provided is not limited to this aspect. For example, as illustrated in FIG. 10, the display unit 48 may be provided between the compression plate 40 and the radiation source 37R. FIG. 10 illustrates an example of the aspect in which the display unit 48 is provided on the compression portion 41 of the compression plate 40.

Further, in the above-described embodiment, the aspect in which the control unit 20, the moving mechanism 47, and the display unit 48 of the mammography apparatus 10 and the control unit 50 of the console 12 are an example of the display device according to the present disclosure has been described. However, for example, other devices may have the functions of the display device according to the present disclosure. For example, the control unit 20 may have the functions of the control unit 50.

Further, in the above-described embodiment, for example, the following various processors can be used as the hardware structure of processing units performing various processes such as the movement control unit 60 and the display control unit 62. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In addition, in the above-described embodiment, the aspect in which the control program 51 is stored (installed) in the ROM 50B in advance has been described. However, the present disclosure is not limited thereto. The control program 51 may be recorded on a recording medium, such as a compact disc read only memory (CD-ROM), a digital versatile disc read only memory (DVD-ROM), or a universal serial bus (USB) memory, and then provided. In addition, the control program 51 may be downloaded from an external device through a network.

What is claimed is:

1. A display device comprising:
a display unit which is provided between a breast and a radiation source of a mammography apparatus that irradiates the breast compressed by a compression member with radiation from the radiation source to capture a radiographic image and displays auxiliary information for assisting a capture of an image of the breast; and
a moving mechanism which moves the display unit between a position inside an irradiation field of the radiation and a position outside the irradiation field of the radiation.

2. The display device according to claim 1, further comprising:
at least one processor,
wherein the processor is configured to direct the moving mechanism to move the display unit to the position outside the irradiation field before the radiation is emitted from the radiation source.

3. The display device according to claim 1, further comprising:
at least one processor,
wherein the processor is configured to
direct the moving mechanism to move the display unit to the position outside the irradiation field in a case in which the compression of the breast by the compression member is completed.

4. The display device according to claim 1, further comprising:
at least one processor,
wherein the processor is configured to
direct the moving mechanism to move the display unit to the position inside the irradiation field in a case in which the emission of the radiation by the radiation source is stopped.

5. The display device according to claim 1, further comprising:
at least one processor,
wherein the processor is configured to
direct the moving mechanism to locate the display unit at the position outside the irradiation field while the radiation is being emitted from the radiation source.

6. The display device according to claim 1, further comprising:
at least one processor,
wherein the processor is configured to
direct the moving mechanism to locate the display unit at the position inside the irradiation field while the radiation is not being emitted from the radiation source.

7. The display device according to claim 1,
wherein the moving mechanism rotates and moves the display unit between the position inside the irradiation field of the radiation and the position outside the irradiation field of the radiation.

8. The display device according to claim 1,
wherein the moving mechanism moves the display unit between the position inside the irradiation field of the radiation and the position outside the irradiation field of the radiation in a direction intersecting a direction in which the radiation is emitted.

9. The display device according to claim 1,
wherein the display unit is provided in the compression member.

10. The display device according to claim 1,
wherein the display unit is provided between the compression member and the radiation source.

11. The display device according to claim 1,
wherein the auxiliary information displayed on the display unit is switched according to at least one of a compression pressure of the compression member against the breast or a height of the compression member.

12. The display device according to claim 1,
wherein the auxiliary information is at least one of information indicating the compression pressure of the compression member against an opposite breast of the same subject with the breast in a case in which an image of the opposite breast is captured by the mammography apparatus, information indicating a thickness of the opposite breast compressed by the compression member, or a radiographic image of the opposite breast.

13. A non-transitory computer-readable storage medium storing a control program that causes a computer to execute a process comprising:
performing control to move a display unit, which is provided between a breast and a radiation source of a mammography apparatus that irradiates the breast compressed by a compression member with radiation from the radiation source to capture a radiographic image and displays auxiliary information for assisting a capture of an image of the breast, between a position inside an irradiation field of the radiation and a position outside the irradiation field of the radiation.

* * * * *